(12) United States Patent
Casanova et al.

(10) Patent No.: US 8,636,794 B2
(45) Date of Patent: Jan. 28, 2014

(54) GRAFTS AND STENT GRAFTS HAVING A RADIOPAQUE MARKER

(75) Inventors: Michael Casanova, Scottsdale, AZ (US); Chandrashekhar Prabhakar Pathak, Phoenix, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 1538 days.

(21) Appl. No.: 12/092,636

(22) PCT Filed: Nov. 9, 2006

(86) PCT No.: PCT/US2006/060702
§ 371 (c)(1),
(2), (4) Date: Sep. 12, 2008

(87) PCT Pub. No.: WO2007/056761
PCT Pub. Date: May 18, 2007

(65) Prior Publication Data
US 2011/0125253 A1    May 26, 2011

Related U.S. Application Data

(60) Provisional application No. 60/734,725, filed on Nov. 9, 2005.

(51) Int. Cl.
*A61F 2/06* (2013.01)

(52) U.S. Cl.
USPC .......................... 623/1.34; 623/1.15; 623/1.13

(58) Field of Classification Search
CPC ..................................... A61F 2/91; A61F 2/82
USPC ................................................ 623/1.15, 1.34
IPC ................................................. A61F 2/06,2/82
See application file for complete search history.

(56) References Cited

U.S. PATENT DOCUMENTS

| | | |
|---|---|---|
| 3,105,492 A | 10/1963 | Jeckel |
| 3,677,800 A | 7/1972 | Wright |
| 3,953,566 A | 4/1976 | Gore |
| 3,962,153 A | 6/1976 | Gore |
| 4,130,904 A | 12/1978 | Whalen |
| 4,226,886 A | 10/1980 | Lakes |
| RE31,618 E | 7/1984 | Mano et al. |
| 4,550,447 A | 11/1985 | Seiler, Jr. et al. |
| 4,604,762 A | 8/1986 | Robinson |
| 4,619,641 A | 10/1986 | Schanzer |

(Continued)

FOREIGN PATENT DOCUMENTS

| | | |
|---|---|---|
| CA | 2620487 A1 | 3/2007 |
| EP | 0203833 A1 | 12/1986 |

(Continued)

OTHER PUBLICATIONS

EP 05855344.7 filed Dec. 28, 2005 Extended European Search Report dated Aug. 14, 2012.

(Continued)

*Primary Examiner* — Jason-Dennis Stewart
(74) *Attorney, Agent, or Firm* — Rutan & Tucker, LLP

(57) ABSTRACT

A graft device comprising a layer of synthetic non-metallic material having a first surface and a second surface spaced apart from the first surface. The device further, includes a radiopaque marker at least partially embedded in the layer.

20 Claims, 6 Drawing Sheets

(56) References Cited

U.S. PATENT DOCUMENTS

| | | | |
|---|---|---|---|
| 4,718,907 A | 1/1988 | Karwoski et al. | |
| 4,731,073 A | 3/1988 | Robinson | |
| 4,733,665 A | 3/1988 | Palmaz | |
| 4,739,013 A | 4/1988 | Pinchuk | |
| 4,743,252 A | 5/1988 | Martin, Jr. et al. | |
| 4,810,749 A | 3/1989 | Pinchuk | |
| 4,816,339 A | 3/1989 | Tu et al. | |
| 4,857,069 A | 8/1989 | Kira | |
| 4,955,296 A | 9/1990 | Barlow | |
| 4,955,899 A | 9/1990 | Della Corna et al. | |
| 4,973,609 A | 11/1990 | Browne | |
| 4,990,138 A | 2/1991 | Bacich et al. | |
| 5,024,671 A | 6/1991 | Tu et al. | |
| 5,028,597 A | 7/1991 | Kodama et al. | |
| 5,061,276 A | 10/1991 | Tu et al. | |
| 5,102,402 A | 4/1992 | Dror et al. | |
| 5,116,360 A | 5/1992 | Pinchuk et al. | |
| 5,133,742 A | 7/1992 | Pinchuk | |
| 5,148,806 A | 9/1992 | Fukui et al. | |
| 5,152,782 A | 10/1992 | Kowligi et al. | |
| 5,192,310 A | 3/1993 | Herweck et al. | |
| 5,201,314 A | 4/1993 | Bosley, Jr. et al. | |
| 5,229,431 A | 7/1993 | Pinchuk | |
| 5,269,810 A | 12/1993 | Hull et al. | |
| 5,319,059 A | 6/1994 | Neuenschwander et al. | |
| 5,320,100 A * | 6/1994 | Herweck et al. | 600/431 |
| 5,354,329 A | 10/1994 | Whalen | |
| 5,453,235 A | 9/1995 | Calcote et al. | |
| 5,462,781 A | 10/1995 | Zukowski | |
| 5,464,438 A | 11/1995 | Menaker | |
| 5,507,769 A | 4/1996 | Marin et al. | |
| 5,516,480 A | 5/1996 | Krall et al. | |
| 5,527,353 A | 6/1996 | Schmitt | |
| 5,556,426 A | 9/1996 | Popadiuk et al. | |
| 5,571,166 A | 11/1996 | Dinh et al. | |
| 5,605,696 A | 2/1997 | Eury et al. | |
| 5,607,442 A * | 3/1997 | Fischell et al. | 623/1.18 |
| 5,607,478 A | 3/1997 | Lentz et al. | |
| 5,609,624 A | 3/1997 | Kalis | |
| 5,620,763 A | 4/1997 | House et al. | |
| 5,628,782 A | 5/1997 | Myers et al. | |
| 5,628,786 A | 5/1997 | Banas et al. | |
| 5,641,373 A | 6/1997 | Shannon et al. | |
| 5,641,443 A | 6/1997 | Calcote et al. | |
| 5,665,114 A | 9/1997 | Weadock et al. | |
| 5,700,287 A | 12/1997 | Myers et al. | |
| 5,707,386 A | 1/1998 | Schnepp-Pesch et al. | |
| 5,711,960 A | 1/1998 | Shikinami | |
| 5,716,393 A | 2/1998 | Lindenberg et al. | |
| 5,716,395 A | 2/1998 | Myers et al. | |
| 5,716,660 A | 2/1998 | Weadock et al. | |
| 5,769,884 A | 6/1998 | Solovay | |
| 5,800,510 A | 9/1998 | Schmitt | |
| 5,800,512 A | 9/1998 | Lentz et al. | |
| 5,817,017 A | 10/1998 | Young et al. | |
| 5,824,042 A * | 10/1998 | Lombardi et al. | 623/1.13 |
| 5,824,050 A | 10/1998 | Karwoski et al. | |
| 5,827,327 A | 10/1998 | McHaney et al. | |
| 5,840,240 A | 11/1998 | Stenoien et al. | |
| 5,843,171 A | 12/1998 | Campbell et al. | |
| 5,843,173 A | 12/1998 | Shannon et al. | |
| 5,851,229 A | 12/1998 | Lentz et al. | |
| 5,851,230 A | 12/1998 | Weadock et al. | |
| 5,860,999 A | 1/1999 | Schnepp-Pesch et al. | |
| 5,861,026 A | 1/1999 | Harris et al. | |
| 5,866,217 A | 2/1999 | Stenoien et al. | |
| 5,893,840 A | 4/1999 | Hull et al. | |
| 5,897,587 A | 4/1999 | Martakos et al. | |
| 5,904,967 A | 5/1999 | Ezaki et al. | |
| 5,910,168 A | 6/1999 | Myers et al. | |
| 5,931,865 A | 8/1999 | Silverman et al. | |
| 5,972,027 A | 10/1999 | Johnson | |
| 5,976,169 A | 11/1999 | Imran | |
| 5,976,192 A | 11/1999 | McIntyre et al. | |
| 6,001,125 A | 12/1999 | Golds et al. | |
| 6,004,667 A | 12/1999 | Sakurada et al. | |
| 6,010,529 A | 1/2000 | Herweck et al. | |
| 6,019,787 A | 2/2000 | Richard et al. | |
| 6,019,788 A | 2/2000 | Butters et al. | |
| 6,022,335 A | 2/2000 | Ramadan | |
| 6,027,779 A | 2/2000 | Campbell et al. | |
| 6,036,724 A | 3/2000 | Lentz et al. | |
| 6,039,755 A | 3/2000 | Edwin et al. | |
| 6,042,666 A | 3/2000 | Karwoski et al. | |
| 6,048,362 A | 4/2000 | Berg | |
| 6,053,939 A | 4/2000 | Okuda et al. | |
| 6,053,941 A | 4/2000 | Lindenberg et al. | |
| 6,053,943 A | 4/2000 | Edwin et al. | |
| 6,056,970 A | 5/2000 | Greenawalt et al. | |
| 6,080,198 A | 6/2000 | Lentz et al. | |
| 6,099,557 A | 8/2000 | Schmitt | |
| 6,102,884 A | 8/2000 | Squitieri | |
| 6,120,532 A | 9/2000 | Goldfarb | |
| 6,124,523 A | 9/2000 | Banas et al. | |
| 6,162,244 A | 12/2000 | Braun et al. | |
| 6,174,330 B1 * | 1/2001 | Stinson | 623/1.34 |
| 6,187,038 B1 | 2/2001 | Sullivan et al. | |
| 6,187,039 B1 | 2/2001 | Hiles et al. | |
| 6,187,054 B1 | 2/2001 | Colone et al. | |
| 6,190,590 B1 | 2/2001 | Randall et al. | |
| 6,200,338 B1 | 3/2001 | Solomon et al. | |
| 6,203,568 B1 | 3/2001 | Lombardi | |
| 6,203,735 B1 | 3/2001 | Edwin et al. | |
| 6,214,839 B1 | 4/2001 | Gutterer | |
| 6,221,101 B1 | 4/2001 | Harris et al. | |
| 6,253,769 B1 | 7/2001 | LaFontaine et al. | |
| 6,261,257 B1 | 7/2001 | Uflacker et al. | |
| 6,267,834 B1 | 7/2001 | Shannon et al. | |
| 6,270,523 B1 | 8/2001 | Herweck et al. | |
| 6,273,908 B1 | 8/2001 | Ndondo-Lay | |
| 6,273,912 B1 | 8/2001 | Scholz et al. | |
| 6,285,739 B1 | 9/2001 | Rudin et al. | |
| 6,287,337 B1 | 9/2001 | Martakos et al. | |
| 6,290,729 B1 | 9/2001 | Slepian et al. | |
| 6,306,166 B1 | 10/2001 | Barry et al. | |
| 6,315,791 B1 | 11/2001 | Gingras et al. | |
| 6,319,279 B1 | 11/2001 | Shannon et al. | |
| 6,328,762 B1 | 12/2001 | Anderson et al. | |
| 6,355,063 B1 | 3/2002 | Calcote | |
| 6,368,347 B1 | 4/2002 | Maini et al. | |
| 6,379,381 B1 | 4/2002 | Hossainy et al. | |
| 6,383,214 B1 | 5/2002 | Banas et al. | |
| 6,383,215 B1 | 5/2002 | Sass | |
| 6,398,806 B1 | 6/2002 | You | |
| 6,416,537 B1 | 7/2002 | Martakos et al. | |
| 6,426,114 B1 | 7/2002 | Troczynski et al. | |
| 6,428,571 B1 | 8/2002 | Lentz et al. | |
| 6,436,135 B1 | 8/2002 | Goldfarb | |
| 6,443,981 B1 | 9/2002 | Colone et al. | |
| 6,451,047 B2 | 9/2002 | McCrea et al. | |
| 6,488,701 B1 | 12/2002 | Nolting et al. | |
| 6,514,196 B1 | 2/2003 | Sullivan et al. | |
| 6,534,084 B1 | 3/2003 | Vyakarnam et al. | |
| 6,547,820 B1 | 4/2003 | Staudenmeier | |
| 6,572,647 B1 | 6/2003 | Supper et al. | |
| 6,589,278 B1 | 7/2003 | Harris et al. | |
| 6,589,468 B1 | 7/2003 | Schmitt | |
| 6,596,023 B1 | 7/2003 | Nunez et al. | |
| 6,602,287 B1 | 8/2003 | Millare et al. | |
| 6,660,301 B1 | 12/2003 | Vogel et al. | |
| 6,663,664 B1 | 12/2003 | Pacetti | |
| 6,673,102 B1 | 1/2004 | Vonesh et al. | |
| 6,676,700 B1 | 1/2004 | Jacobs et al. | |
| 6,712,919 B2 | 3/2004 | Ruefer et al. | |
| 6,716,239 B2 | 4/2004 | Sowinski et al. | |
| 6,719,783 B2 | 4/2004 | Lentz et al. | |
| 6,726,696 B1 | 4/2004 | Houser et al. | |
| 6,726,923 B2 | 4/2004 | Iyer et al. | |
| 6,730,324 B2 | 5/2004 | Troczynski et al. | |
| 6,746,480 B2 | 6/2004 | Scholz et al. | |
| 6,756,007 B2 | 6/2004 | Pletzer et al. | |
| 6,786,920 B2 | 9/2004 | Shannon et al. | |
| 6,790,226 B2 | 9/2004 | Edwin et al. | |
| 6,797,217 B2 | 9/2004 | McCrea et al. | |

(56) References Cited

U.S. PATENT DOCUMENTS

| | | | |
|---|---|---|---|
| 6,803,069 B2 | 10/2004 | Patnaik et al. | |
| 6,814,753 B2 | 11/2004 | Schmitt | |
| 6,821,295 B1 | 11/2004 | Farrar | |
| 6,827,737 B2 | 12/2004 | Hill et al. | |
| 6,863,686 B2 | 3/2005 | Shannon et al. | |
| 6,926,735 B2 | 8/2005 | Henderson | |
| 7,083,640 B2 | 8/2006 | Lombardi et al. | |
| 7,244,271 B2 | 7/2007 | Lentz et al. | |
| 8,043,364 B2 | 10/2011 | Lombardi et al. | |
| 8,066,758 B2 | 11/2011 | Bogert et al. | |
| 8,313,524 B2 | 11/2012 | Edwin et al. | |
| 2001/0018609 A1 | 8/2001 | Smith | |
| 2001/0021870 A1 | 9/2001 | Edwin et al. | |
| 2001/0029382 A1 | 10/2001 | Bowman et al. | |
| 2002/0055097 A1 | 5/2002 | Polyak et al. | |
| 2002/0065546 A1 | 5/2002 | Machan et al. | |
| 2002/0065552 A1 | 5/2002 | Jayaraman et al. | |
| 2002/0091439 A1 | 7/2002 | Baker et al. | |
| 2002/0095157 A1 | 7/2002 | Bowman | |
| 2002/0095205 A1 | 7/2002 | Edwin et al. | |
| 2002/0127261 A1 | 9/2002 | Risbud et al. | |
| 2002/0138048 A1 | 9/2002 | Tuch | |
| 2002/0138136 A1 | 9/2002 | Chandresekaran et al. | |
| 2002/0169465 A1 | 11/2002 | Bowman et al. | |
| 2002/0193869 A1 | 12/2002 | Dang | |
| 2002/0198559 A1 | 12/2002 | Mistry et al. | |
| 2003/0004559 A1 | 1/2003 | Lentz et al. | |
| 2003/0004563 A1 | 1/2003 | Jackson et al. | |
| 2003/0017775 A1 | 1/2003 | Sowinski et al. | |
| 2003/0027775 A1 | 2/2003 | Wallace | |
| 2003/0028204 A1 | 2/2003 | Li et al. | |
| 2003/0028240 A1 | 2/2003 | Nolting et al. | |
| 2003/0060871 A1 | 3/2003 | Hill et al. | |
| 2003/0100859 A1 | 5/2003 | Henderson et al. | |
| 2003/0139799 A1 | 7/2003 | Ley et al. | |
| 2003/0139806 A1 | 7/2003 | Haverkost et al. | |
| 2003/0149471 A1 | 8/2003 | Briana et al. | |
| 2003/0176915 A1 | 9/2003 | Wright et al. | |
| 2003/0204242 A1 | 10/2003 | Zarins et al. | |
| 2003/0216699 A1 | 11/2003 | Falotico | |
| 2003/0224032 A1 | 12/2003 | Read et al. | |
| 2004/0015228 A1 | 1/2004 | Lombardi et al. | |
| 2004/0024442 A1 | 2/2004 | Sowinski et al. | |
| 2004/0024456 A1 | 2/2004 | Brown et al. | |
| 2004/0033364 A1 | 2/2004 | Spiridigliozzi et al. | |
| 2004/0049264 A1 | 3/2004 | Sowinski et al. | |
| 2004/0054406 A1 | 3/2004 | Dubson et al. | |
| 2004/0064181 A1 | 4/2004 | Harris et al. | |
| 2004/0076656 A1 | 4/2004 | Pavesio et al. | |
| 2004/0078090 A1 | 4/2004 | Binette et al. | |
| 2004/0082989 A1 | 4/2004 | Cook et al. | |
| 2004/0117006 A1 | 6/2004 | Lewis et al. | |
| 2004/0117015 A1* | 6/2004 | Biscup | 623/16.11 |
| 2004/0122507 A1 | 6/2004 | Henderson | |
| 2004/0122509 A1 | 6/2004 | Brodeur | |
| 2004/0127977 A1 | 7/2004 | Shanley | |
| 2004/0146546 A1 | 7/2004 | Gravett et al. | |
| 2004/0148013 A1 | 7/2004 | Epstein et al. | |
| 2004/0164445 A1 | 8/2004 | Nieman et al. | |
| 2004/0167572 A1 | 8/2004 | Roth et al. | |
| 2004/0182511 A1 | 9/2004 | Rakos et al. | |
| 2004/0186552 A1* | 9/2004 | St. Pierre | 623/1.15 |
| 2004/0186553 A1 | 9/2004 | Yan | |
| 2004/0193242 A1 | 9/2004 | Lentz et al. | |
| 2004/0210302 A1 | 10/2004 | Scholz et al. | |
| 2004/0215337 A1 | 10/2004 | Hain et al. | |
| 2004/0232588 A1 | 11/2004 | Edwin et al. | |
| 2004/0236400 A1 | 11/2004 | Edwin et al. | |
| 2004/0244442 A1 | 12/2004 | Shiao et al. | |
| 2005/0002981 A1 | 1/2005 | Lahtinen et al. | |
| 2005/0004653 A1* | 1/2005 | Gerberding et al. | 623/1.13 |
| 2005/0004661 A1 | 1/2005 | Lewis et al. | |
| 2005/0010297 A1 | 1/2005 | Watson et al. | |
| 2005/0015138 A1 | 1/2005 | Schuessler et al. | |
| 2005/0015154 A1 | 1/2005 | Lindsey et al. | |
| 2005/0055097 A1 | 3/2005 | Grunberg et al. | |
| 2005/0060020 A1 | 3/2005 | Jenson | |
| 2005/0064224 A1 | 3/2005 | Bavaro et al. | |
| 2005/0096721 A1 | 5/2005 | Mangin et al. | |
| 2005/0186243 A1* | 8/2005 | Hunter et al. | 424/423 |
| 2005/0246012 A1 | 11/2005 | Henderson | |
| 2005/0283226 A1* | 12/2005 | Haverkost | 623/1.15 |
| 2006/0058867 A1 | 3/2006 | Thistle et al. | |
| 2006/0116755 A1 | 6/2006 | Stinson | |
| 2006/0259133 A1 | 11/2006 | Sowinski et al. | |
| 2007/0038290 A1* | 2/2007 | Huang et al. | 623/1.16 |
| 2007/0123968 A1 | 5/2007 | Weinberg | |
| 2007/0204445 A1 | 9/2007 | Hood et al. | |
| 2007/0244539 A1 | 10/2007 | Lentz et al. | |
| 2008/0027534 A1 | 1/2008 | Edwin et al. | |
| 2009/0171436 A1 | 7/2009 | Casanova et al. | |
| 2010/0179642 A1 | 7/2010 | Bogert et al. | |
| 2010/0268321 A1 | 10/2010 | McDermott et al. | |
| 2011/0076315 A1 | 3/2011 | Casanova et al. | |
| 2012/0061001 A1 | 3/2012 | Bogert et al. | |
| 2013/0071550 A1 | 3/2013 | Edwin et al. | |

FOREIGN PATENT DOCUMENTS

| | | |
|---|---|---|
| EP | 0734721 A3 | 1/1997 |
| EP | 1371345 A2 | 12/2003 |
| EP | 1922025 A4 | 4/2012 |
| JP | 05-317408 A | 12/1993 |
| JP | 2000501961 A | 2/2000 |
| JP | 2000167063 A | 6/2000 |
| JP | 2000171595 A | 6/2000 |
| JP | 2000217903 A | 8/2000 |
| JP | 2002501779 | 1/2002 |
| JP | 2002540854 | 12/2002 |
| JP | 2003511196 A | 3/2003 |
| JP | 2003284781 A | 10/2003 |
| JP | 2004-537344 A | 12/2004 |
| JP | 2006511283 A | 4/2006 |
| JP | 2006514557 A | 5/2006 |
| JP | 2006527630 A | 12/2006 |
| JP | 2009506875 A | 2/2009 |
| JP | 5118042 | 10/2012 |
| WO | 9003036 A1 | 3/1990 |
| WO | 9323090 A1 | 11/1993 |
| WO | 9703812 A1 | 2/1997 |
| WO | 9721401 A1 | 6/1997 |
| WO | 9812990 A1 | 4/1998 |
| WO | 9826731 A2 | 6/1998 |
| WO | 0128456 A1 | 4/2001 |
| WO | 0149340 A1 | 7/2001 |
| WO | 0158504 | 8/2001 |
| WO | 02055121 A1 | 7/2002 |
| WO | 02055122 A1 | 7/2002 |
| WO | 2004011055 A2 | 2/2004 |
| WO | 2004021931 A1 | 3/2004 |
| WO | 2004096307 A1 | 11/2004 |
| WO | 2006133373 A3 | 5/2007 |
| WO | 2007030512 A3 | 6/2007 |
| WO | 2008063780 A3 | 12/2008 |

OTHER PUBLICATIONS

EP 06839788.4 filed on Aug. 5, 2008 EP Search Report dated Dec. 28, 2009.

EP 06839788.4 filed on Aug. 5, 2008 Office Action dated Jul. 13, 2010.

James et al, "In Vivo Patency of Endothelial Cell-Lined ePTFE Prostheses in an Ovine Model"; Artif Organs, Aug. 16, 1992 (4):346-53.

JP 2007-530364 filed Aug. 30, 2005 Office Action dated Oct. 19, 2010.

JP 2008-516811 filed Dec. 28, 2005 Office Action dated Mar. 28, 2011.

JP 2008-540337 filed Apr. 27, 2006 Office Action dated Apr. 6, 2012.

JP 2008-540337 filed Apr. 27, 2006 Office Action dated Nov. 24, 2011.

JP 2008-540338 filed Apr. 27, 2006 Office Action dated Sep. 30, 2011.

(56) References Cited

OTHER PUBLICATIONS

Kohler et al, "Dialysis Access Failure: A Sheep Model of Rapid Stenosis", J Vase Surg., Oct. 30, 1999 (4):744-51.
PCT/US2005/031186 filed Aug. 30, 2005 International Preliminary Report on Patentability dated Feb. 28, 2007.
PCT/US2005/031186 filed Aug. 30, 2005 Search Report dated Feb. 6, 2007.
PCT/US2005/031186 filed Aug. 30, 2005 Written Opinion dated Feb. 6, 2007.
PCT/US2005/046763 filed Dec. 28, 2005 International Preliminary Report on Patentability dated Dec. 17, 2007.
PCT/US2005/046763 filed Dec. 28, 2005 Search Report dated Apr. 30, 2007.
PCT/US2005/046763 filed Dec. 28, 2005 Written Opinion dated Apr. 30, 2007.
PCT/US2006/060704 filed on Nov. 9, 2006 International Preliminary Report on Patentability dated May 14, 2006.
PCT/US2006/060704 filed on Nov. 9, 2006 Search Report dated Nov. 1, 2007.
PCT/US2006/060704 filed on Nov. 9, 2006 Written Opinion dated Nov. 1, 2007.
Tillman et al, "Platelet Function and Coagulation Parameters in Sheep During Experimental Vascular Surgery", Lab Anim Sci., 1981 Jun.; 31 (3):263-7.
U.S. Appl. No. 11/661,250, filed Mar. 27, 2007 Final Office Action dated Oct. 14, 2009.
U.S. Appl. No. 11/661,250, filed Mar. 27, 2007 Non-Final Office Action dated Apr. 1, 2009.
U.S. Appl. No. 11/661,250, filed Mar. 27, 2007 Non-Final Office Action dated Apr. 13, 2012.
U.S. Appl. No. 11/661,250, filed Mar. 27, 2007 Non-Final Office Action dated Sep. 18, 2008.
U.S. Appl. No. 11/661,250, filed Mar. 27, 2007 Notice of Allowance dated Jul. 27, 2012.
U.S. Appl. No. 11/917,135, filed Jan. 17, 2008 Final Office Action dated May 9, 2011.
U.S. Appl. No. 11/917,135, filed Jan. 17, 2008 Non-Final Office Action dated Nov. 26, 2010.
U.S. Appl. No. 12/092,561, filed Sep. 17, 2008 Final Office Action dated Jun. 15, 2012.
U.S. Appl. No. 12/092,561, filed Sep. 17, 2008 Non-Final Office Action dated Jan. 4, 2012.
International Search Report, PCT/US2006/060702.
Written Opinion of the International Search Report, PCT/US2006/060702.
Jan. 12, 2010 European Search Report in EP Application No. EP 06839787.6 filed on Nov. 11, 2006.
Dec. 28, 2007 International Search Report in International Application No. PCT/US2006/060702 filed on Nov. 11, 2006.
Nov. 7, 2007 Written Opinion of the ISA in International Application No. PCT/US2006/060702 filed on Nov. 11, 2006.
May 14, 2008 International Preliminary Report on Patentability in International Application No. PCT/US2006/060702 filed on Nov. 11, 2006.
Bard Peripheral Vascular, Dynaflo Bypass Grafts, Information for Use, Jan. 2005.
Bard Peripheral Vascular, Venaflo™ Vascular Grafts, Information for Use, Oct. 2004.
EP 05855344.7 filed Dec. 28, 2005 Examination Report dated Oct. 26, 2012.
EP 06772602.6 European Search Report dated Jan. 4, 2013.
Graft. 2012. In TheFreeDictionary.com. Retrieved Aug. 22, 2012, from http://www.thefreedictionary.com/graft.
Hakimmehr, Dorna, The effect of organic solvents on sol-gel hydroxyapatite and its application as biocoating, The University of British Columbia, pp. 1-98, Oct. 2001.
Ignjatovic, Nenad, et al., Hydroxyapatite/poly-L-lactide (Collagen) Biocomposite with Poly-L-lactide of Different Molecular Weights, Advanced Engineering Materials, 2, No. 8 (2000), pp. 511-514.
JP Application No. 2008-515934 filed Dec. 7, 2007 Office Action dated Mar. 13, 2012.
JP Application No. 2008-515934 filed Dec. 7, 2007 Office Action dated May 6, 2011.
Masaki, Takahisha, et al., In Vitro Pharmacological Inhibition of Human Vascular Smooth Muscle Cell Proliferation for the Prevention of Hemodialysis Vascular Access Stenosis, Blood Purification, vol. 22, No. 3, pp. 307-312 (2004).
Murase, Katsutoshi et al: "Graft-preserving treatment for vascular graft infected with *Staphylococcus aureus* with antibiotic-releasing porous apatite ceramic in the rabbit", Journal of Vascular Surgery, v. 38, No. 2, Aug. 1, 2003, pp. 368-373.
PCT/US2006/022359 filed Jun. 8, 2006 International Preliminary Report on Patentability dated Dec. 11, 2007.
PCT/US2006/022359 filed Jun. 8, 2006 International Search Report dated Mar. 1, 2007.
PCT/US2006/022359 filed Jun. 8, 2006 Written Opinion dated Mar. 1, 2007.
PCT/US2006/034671 filed Sep. 5, 2006 International Preliminary Report on Patentability dated Mar. 11, 2008.
PCT/US2006/034671 filed Sep. 5, 2006 International Search Report dated Apr. 2, 2007.
PCT/US2006/034671 filed Sep. 5, 2006 Written Opinion dated Apr. 2, 2007.
PCT/US2007/081261 dated Oct. 12, 2007 International Preliminary Report on Patentability dated Apr. 15, 2009.
PCT/US2007/081261 dated Oct. 12, 2007 Search Report dated Sep. 24, 2008.
PCT/US2007/081261 dated Oct. 12, 2007 Written Opinion dated Sep. 24, 2008.
Ravaglioli, A., et al., Performances of Hydroxyapatite Porosity in Contact with Cells and Tissues, Key Engineering Materials, vols. 254-256, pp. 1017-1020 (2004).
U.S. Appl. No. 11/916,813, filed Aug. 27, 2010 Final Office Action dated Jan. 10, 2013.
U.S. Appl. No. 11/916,813, filed Aug. 27, 2010 Non-Final Office Action dated Apr. 9, 2012.
U.S. Appl. No. 11/916,813, filed Aug. 27, 2010 Non-Final Office Action dated Aug. 30, 2012.
U.S. Appl. No. 12/065,888, filed Jun. 9, 2010 Non-Final Office Action dated Jul. 17, 2012.
U.S. Appl. No. 12/444,568, filed Apr. 6, 2009 Advisory Action dated Oct. 16, 2012.
U.S. Appl. No. 12/444,568, filed Apr. 6, 2009 Final Office Action dated Apr. 12, 2012.
U.S. Appl. No. 12/444,568, filed Apr. 6, 2009 Non-Final Office Action dated Sep. 21, 2011.
W. L. Gore & Associates, Inc., Gore-Tex® Intering Vascular Graft Advertisement, 2 pages, Aug. 2004.
W. L. Gore & Associates, Inc., The Highway of Life Advertisement, 2 pages, May 2004.
EP 05794340.9 European Search Report dated Apr. 25, 2013.
U.S. Appl. No. 11/916,813, filed Aug. 27, 2010 Advisory Action dated Apr. 17, 2013.
U.S. Appl. No. 12/065,888, filed Jun. 9, 2010 Final Office Action dated Mar. 7, 2013.

\* cited by examiner

GRAFTS AND STENT GRAFTS HAVING A RADIOPAQUE MARKER

PRIORITY DATA AND INCORPORATION BY REFERENCE

This is a National Stage application under 35 U.S.C. 371 of International Application No. PCT/US 2006/060702, filed Nov. 9, 2006, which claims the benefit of priority to U.S. Provisional Patent Application No. 60/734,725 filed Nov. 9, 2005, and each of which is incorporated by reference in its entirety.

TECHNICAL FIELD

The present invention relates generally to medical devices, and more particularly to a radiopaque marker for implantable devices.

BACKGROUND OF THE INVENTION

Unless specifically defined, the terms "Radio-opaque" or "Radiopaque" have same meaning. Stents, artificial grafts, and related endoluminal devices are currently used by medical practitioners to treat tubular body vessels or ducts that become so narrowed (stenosed) that flow of blood or other biological fluids is restricted. Such narrowing (stenosis) occurs, for example, as a result of the disease process known as arteriosclerosis. While stents are most often used to "prop open" blood vessels, they can also be used to reinforce collapsed or narrowed tubular structures in the respiratory system, the reproductive system, bile or liver ducts or any other tubular body structure.

Vascular grafts made of polytetrafluoroethylene (PTFE) are typically used to replace or repair damaged or occluded blood vessels within the body. However, they may require additional means for anchoring the graft within the blood vessel, such as sutures, clamps, or similarly functioning elements to overcome retraction. Stents have been used in combination with grafts to provide endovascular prostheses which are capable of maintaining their fit against blood vessel walls. The use of grafts along with stents also serves to overcome a problem found with stents where smooth muscle cells and other tissues can grow through the stent's mesh-like openings, resulting in restenosis of the vessel.

PTFE has proven unusually advantageous as a material from which to fabricate blood vessel grafts or prostheses, because PTFE is extremely biocompatible, causing little or no immunogenic reaction when placed within the human body. In its preferred form, expanded PTFE (ePTFE), the material is light, porous and readily colonized by living cells so that it becomes a permanent part of the body. The process of making ePTFE of vascular graft grade is well known to one of ordinary skill in the art. Suffice it to say that the critical step in this process is the expansion of PTFE into ePTFE. This expansion represents a controlled longitudinal stretching in which the PTFE is stretched to several hundred percent of its original length. Examples of ePTFE grafts are shown and described in U.S. Pat. Nos. 5,641,443; 5,827,327; 5,861,026; 5,641,443; 5,827,327; 6,203,735; 6,221,101; 6,436,135; and 6,589,278, each of which is incorporated in its entirety by reference. Grafts made from materials other than ePTFE that have been utilized include, for example, Dacron mesh reinforced umbilical tissues, bovine collagen, polyester knitted collagen, tricot knitted polyester collagen impregnated, and polyurethane (available under the trademark Vectra®).

Stent grafts are a prosthetic device designed to maintain the patency of various vessels in the body, including the tracheobronchial tree. The device may include a balloon expandable stent encapsulated with ePTFE or alternatively a self-expanding Nitinol stent encapsulated with ePTFE and pre-loaded on a flexible delivery system. One example of the latter is known commercially as "Fluency®," which is marketed by C.R. Bard Peripheral Vascular Inc. Examples of such stent-graft is shown and described in U.S. Pat. Nos. 6,053,941; 6,124,523; 6,383,214; 6,451,047; and 6,797,217, each of which is incorporated in its entirety by reference. The field of covering stents with polymeric coatings and ePTFE in particular has been substantially explored by those skilled in the art. One popular way of covering the stent with ePTFE material is to encapsulate it within two layers of ePTFE which are subsequently fused together by heat in places where the two layers are in contact through openings in the stent wall. This provides a solid one-piece device that can be expanded and contracted without an ePTFE layer delaminating.

Implantation of a graft or an encapsulated stent into the vasculature of a patient involves very precise techniques. Generally, the device is guided to the diseased or damaged portion of a blood vessel via an implantation apparatus that deploys the graft or the encapsulated stent at the desired location. In order to pinpoint the location during deployment, the medical specialist will generally utilize a fluoroscope to observe the deployment by means of X rays. Deployment of an encapsulated stent at an unintended location can result in immediate trauma, as well as increasing the invasiveness associated with multiple deployment attempts and/or relocation of a deployed device. In addition, visualization of the implanted device is essential for implantation, follow-up inspection and treatment. Accordingly, in order to implant the encapsulated stent using fluoroscopy, some portion of the stent, graft or implantation device should be radiopaque.

Stents that are implanted and expanded within a blood vessel using a balloon catheter can be located by fluoroscopy because the balloon catheter can have radiopaque features incorporated therein that may be used as a visual marker. However, if the balloon moves after expansion of the stent, correct placement of the stent, in the absence of a radiopaque marker incorporated into the stent, cannot be confirmed. A self-expanding stent can be generally delivered to the damaged or diseased site via a constraining member in the form of a catheter or sheath and can be deployed by removing the constraining member. In order to direct the delivery device and the self-expanding stent to the precise location for deployment, the radiopacity must be incorporated into the device or the constraining member to confirm the correct placement within the vessel.

In addition to visually verifying the location of the implanted stent or graft, it may be necessary to visually verify the orientation of the graft or stent, and/or visually determine if the implant has been twisted or kinked. A properly configured radiopaque marker can facilitate meeting these visual needs. Moreover, radiopaque markers incorporated into the material of a graft or encapsulated stent can provide an alternative to exposed "spoon" type markers that can contact areas of the blood vessel being treated.

DISCLOSURE OF INVENTION

A preferred embodiment according to the present invention provides a graft device comprising a layer of synthetic non-metallic material having a first surface and a second surface spaced apart from the first surface. The device further includes a radiopaque marker at least partially embedded in the layer. In one embodiment, the radiopaque marker is about twenty to sixty percent (20-60%) tantalum powder. Alternatively, the radiopaque marker is about 20% to about 60% Barium Sulfate.

In another preferred embodiment, a graft device comprises a layer of synthetic non-metallic material having a first surface and a second surface spaced apart from the first surface. The device further includes a radio-opaque ink printed on at least one of the first and second surfaces of the synthetic non-metallic material.

In another embodiment, the marker preferably has a color so as to be visible to the naked eye as well as being radio-opaque. In one preferred embodiment, radio-opaque material Barium Sulfate material is mixed with biocompatible dye or pigment to make a colored as well as radio-opaque marker.

In yet another embodiment, a graft device comprises a stent frame, a synthetic non-metallic material that surrounds a portion of the stent frame, and a radiopaque strip embedded in the non-metallic material.

Another embodiment according to the present invention provides a method of forming a graft device. The method comprises extruding a synthetic non-metallic material so as to form a member having a first surface and a second surface spaced apart from the first surface. Extruding the non-metallic material includes extruding a radiopaque material at least partially embedded in the non-metallic material to form the device.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention. It should be understood that the preferred embodiments are examples of the invention as provided by the appended claims.

MODE(S) FOR CARRYING OUT THE INVENTION

Figure 1:
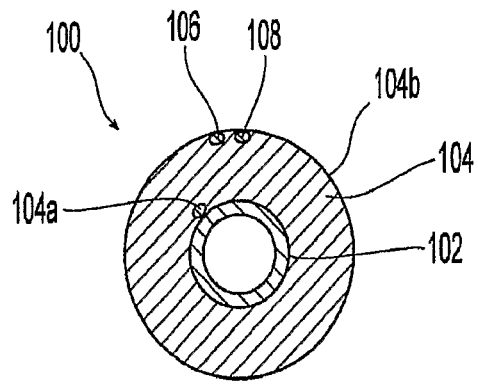
FIG. 1 illustrates a cross-section of a preferred graft device.

FIGS. 1-8 illustrate the preferred embodiments. Shown in FIG. 1 is a cross-section of one of the preferred embodiments of a graft device 100 having at least one radiopaque marker 106 embedded in an outer surface 104B of the device 100. Alternatively or in addition to, one or more radiopaque markers 102, 108 can be provided on the inner surface 104A, outer surface 104B or be dispersed or integrated with the graft material 104 of the device 100 between the inner surface 104A and the outer surface 104B.

The device 100 can be made from a graft material 104 which can be a non-metallic material. Specifically, the non-metallic material 104 can include a synthetic fiber or fabric material such as, for example, Dacron, polyester, PTFE, ePTFE, polyurethane, polyurethane-urea, siloxane, and combinations thereof with an appropriate amount of additives added therein such as, for example, bio-active agents. In the preferred embodiments, the graft material 104 is expanded polytetrafluoroethylene or "ePTFE."

The ePTFE material for graft 104 can be made by a variety of suitable techniques, one of which is described as follows. A compounding of a polymeric compound is generated by sifting PTFE resin with a suitable amount of lubricant such as, for example, Isopar H, at 15-35% by weight of the PTFE to enable the PTFE to flow through extrusion equipment. The combined PTFE resin and lubricant are then placed in a shaker device and shaken so that the lubricant coats and penetrates each of the PTFE resin particles. The thoroughly mixed combination of PTFE resin and lubricant is then incubated in a warming cabinet overnight which is maintained at a temperature of approximately eighty-five degrees Fahrenheit (85° F.). The incubation period is believed to allow for a further and more equal dispersion of the lubricant throughout the PTFE resin.

If desired, the PTFE resin can be further mixed and heated as part of an optional compounding process. For example, the PTFE resin can be compounded with a suitable hydroxyapatite (HA) material to produce a graft configured for increased biocompatibility and bioactivity in order to, for example, promote endothelial cell growth for the maintenance of graft patency and the reduction of intimal hyperplasia.

Figure 2:
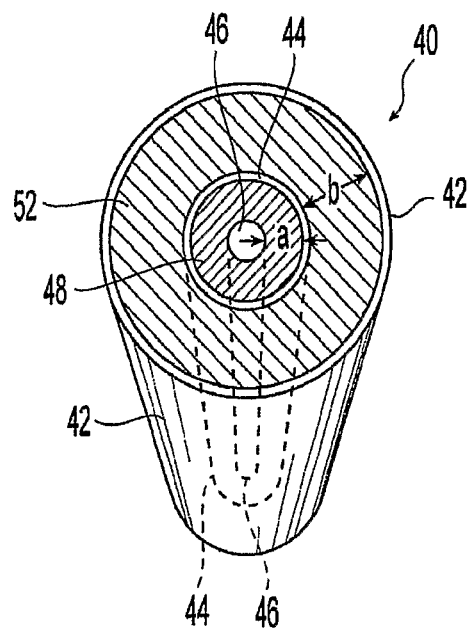
FIG. 2 illustrates a cross-section of a preferred device used in making the graft device of FIG. 1.

The PTFE resin or its compound can be preformed into a compressed cylinder by series of process steps. First, the resin can be poured into an inner barrel of a preformer by directing it through a funnel which is fit to the outside of the inner barrel. FIG. 2 illustrates a preferred embodiment of a divided preform barrel 40 which can be used in preforming a resin into a compressed cylinder. The divided preform barrel 40 preferably includes an outer hollow cylindrical member 42, an optional inner hollow cylindrical member 44, and a central solid cylindrical member 46. The inner hollow cylindrical member 44 can be concentrically contained within the outer hollow cylindrical member 42. Details of a similar process are shown and described in U.S. Pat. Nos. 5,827,327; 5,641,443; and 6,190,590, each of which is incorporated in its entirety by reference.

The PTFE resin can be poured within a first area 52 located between the outer hollow cylindrical member 42 and a solid cylindrical member 46. The first area 52 can be divided by one or more inner members 44 to define a secondary area 48 for receipt of any optionally added compound such as, for example, an HA compound material.

In one of the preferred embodiments, the outer hollow cylindrical member 42 has a radius greater than the radius of the inner hollow cylindrical member 44. The diameter of the components which comprise the preform barrel 40 will vary depending on the size and type of graft that is being produced. A preferred embodiment of the preform barrel 40 can have a radius of approximately 1.5 inches. The secondary area 48 between the inner hollow cylindrical member 44 and the central solid cylindrical member 46 can have a radius of approximately 0.38 inches, the inner hollow cylindrical member 44 can have a wall thickness of approximately 0.07 inches, and the first area 52 located between the outer hollow cylindrical member 42 and the inner hollow cylindrical member 44 can have a radius of approximately 0.6 inches.

In addition, a radiopaque paste or resin can be partially or fully embedded in a portion of the outer or inner surfaces of the PTFE resin. Preferably, the radiopaque paste can be formed from a tantalum powder. Other radio-opaque materials which could be used include, but are not limited to, tungsten, gold, silver powder, Barium Sulfate and the like. The preferred radio-opaque material is also heat stable so that it can tolerate sintering temperature encountered during graft manufacturing. In one exemplary embodiment, the radio-opaque paste can be formed by mixing 4 grams of ePTFE, 6 grams of tantalum and 2 grams of Isopar-H to produce a mixture containing sixty percent (60%) tantalum. Preferably, substantially all lubricant is evaporated after extrusion and sintering as described herein. Further in the alternative, the radiopaque paste can be formed from a Barium Sulfate mixture. For example, the radiopaque paste can include an ePTFE paste mixed with twenty to forty percent (20-40%) Barium Sulfate. In a preferred embodiment, the radiopaque paste is formed into an elongated strip that can be disposed along the length of the outer surface of the PTFE resin. Alternatively or in addition to, the radiopaque paste can form a plurality of radiopaque elements that can be aligned along the outer surface of the PTFE resin along its length. The radiopaque paste can be formed into any shape or form. For example, the paste can be formed as sutures, threads and other small pieces such as disks disposed anywhere within the PTFE resin. The continuous or elongated strip of radiopaque material can provide the visual cues to the clinician viewing the stent under fluoroscopy such as, for example, location, orientation or kinking.

The assembly of PTFE resin and radiopaque paste markers can then be compressed. The materials are compressed by placing the assembly into the preform barrel 40 on a suitable press such as, for example, shown in FIG. 3 of U.S. Pat. No. 5,827,327. The press used during the compression of the polymeric compound is driven by a suitable power drive, which forces a top member toward a bottom member to compress the material within the divided preform barrel 40. Hollow cylindrical tubes of varying thickness are used to compress the material within the divided preform barrel 40 by slidably reciprocating around the inner hollow cylindrical member 44, the outer hollow cylindrical member 42, and the center solid cylindrical member 46 of the divided preform barrel 40. After compressing the materials contained within the preform barrel 40, the inner cylindrical member 44 (if used), the outer cylindrical member 42, and the center solid cylindrical member 46 of the divided preform barrel 40 are removed to obtain a compressed cylinder of material. Alternatively, the dividers within the preform barrel may be removed prior to compression, without disturbing the interface between the different compounds, and then compressed to form a billet for extrusion. The compressed cylinder of material, or billet, can be co-extruded via a suitable device such as, for example, the extruder shown in FIG. 4 of U.S. Pat. No. 5,827,327. Briefly, the compressed cylinder of material is placed within an extrusion barrel. Force is applied to a ram, which in turn expels pressure on the compressed cylinder of material. The pressure causes the compressed cylinder of material to be extruded around a mandrel, through an extrusion die, and issue as a tubular extrudate. The tubular extrudate can be expanded to increase the porosity or alter the elasticity of the extrudate. After extrusion or expansion, the extrudate can be sintered in accordance with the expansion and sintering procedures undertaken with PTFE grafts which are known to those skilled in the art.

In one embodiment, a PTFE billet can include an optional HA lumenal layer 102 formed with a first outer strip of tantalum paste 106 and a second outer strip of Barium Sulfate paste 108. The billet can be extruded through a suitable extruder at a pressure from about 500 to about 2000 psi. The reduction ratio (i.e., wall thickness of billet to extruded graft thickness) for the billet can be from about 50 to about 350. Table 1 below shows a preferred composition of a PTFE billet by weight.

TABLE 1

| Ref. Number | Formulation | PTFE Resin Weight (g) | Tantalum Weight (g) | Barium Sulfate Weight (g) | Hydroxy-apatite (g) | Lube Weight (g) |
|---|---|---|---|---|---|---|
| 102 | HA luminal layer | 200 | — | — | 50 | 60 |
| 106 | Tantalum line | 4 | 6 | — | — | 2 |
| 108 | Barium Sulfate Line* | 4 | — | 6 | — | 2 |
| — | PTFE base | 500 | | | — | 100 |

*The Barium Sulfate is preferably mixed with 10-200 milligrams (mg.) cobalt blue (CAS no. 1345-16-0) to induce blue color.

The billets can be extruded to form various tubes 1 to 30 millimeters (mm.) in diameter, preferably 5 mm. to 6 mm. in diameter for peripheral vascular graft applications. More preferably, the diameter measured is the inner diameter of the tube. Each extruded tube can be expanded to various lengths to introduce different degrees of porosity in the PTFE material, thereby providing the expanded PTFE or ePTFE. The expanded tubes can be sintered at a suitable sintering temperature to cause the tube to maintain essentially the desired porosity and improve the physical characteristics of the expanded ePTFE. The expansion can potentially reduce the radio-opacity of the extruded material. In general, higher expansion gives reduced radio-opacity and/or visibility to the naked eye. It is preferred to add sufficient radio-opaque material or pigment material to produce a colored marking after expansion so that the graft shows adequate radio-opacity when viewed using medical x-ray imaging equipment. The sintering temperature can be similar to that of standard ePTFE graft processing, which can be from about 200 degrees Fahrenheit to 400 degrees Fahrenheit, and preferably about 300 degrees Fahrenheit. Other techniques to provide for the graft device 100 are shown and described in U.S. Pat. Nos. 5,628,786; 6,053,943; and 6,203,735 and U.S. Patent Application Publication Nos. 2004/0164445; 2004/0232588; and 2004/0236400, each of which is incorporated in its entirety by reference.

In one embodiment, Barium Sulfate as a radio-opaque material is mixed with a biocompatible coloring agent to produce a blue color marking. Many biocompatible coloring agents or their mixtures can be used to produce desired color or shade. Black, blue or green colors are most preferred. Tantalum or tungsten metal provide black color as well as radio-opaque properties. In such case, no coloring agent may be needed. Many biocompatible coloring agents may be used, but colors that withstand high sintering temperature without substantial degradation are preferred. The preferred colored materials include, but are not limited to, cobalt blue, (Phthalocyaninato(2-)) copper, Chromium-cobalt-aluminum oxide, titanium oxide or mixtures thereof and the like.

Again referring to FIG. 1, a tube preferably extruded by the process described above can form the lumenal graft device 100. The graft device 100 further preferably includes one or more elongated radiopaque markers or strips 106, 108 embedded in a first inner surface 104A, a second surface 104B or in the material 104 between the first and second surfaces 104A, 104B. More specifically, extrusion of the PTFE resin and the radiopaque marker provides for the device 100 with an ePTFE layer 104 with first surface 104A and second surface 104B. In a preferred embodiment, the device 100 includes at least one elongated portion 106 of radiopaque material on the outer surface 104B in which the radiopaque material is made of either tantalum powder or Barium Sulfate. The elongated portion 106 further preferably forms a continuous strip that runs along the length of the device 10. Alternatively, the graft device 100 can have one or more radiopaque elements, in any orientation line provided by the device 100 to improve visibility in a suitable imaging technique (e.g., x-ray imaging). More specifically, the radiopaque material can form a series of radiopaque elements (not shown) aligned along the length of the outer surface 104B of the device 100.

Figure 3:
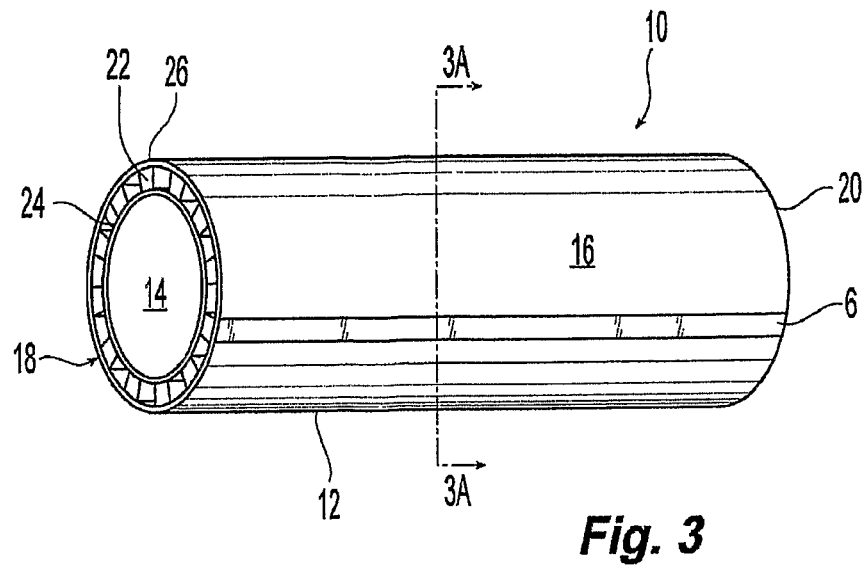
FIG. 3 is a perspective view of an illustrative embodiment of a stent graft having a longitudinal radiopaque marker.
Figure 3B:
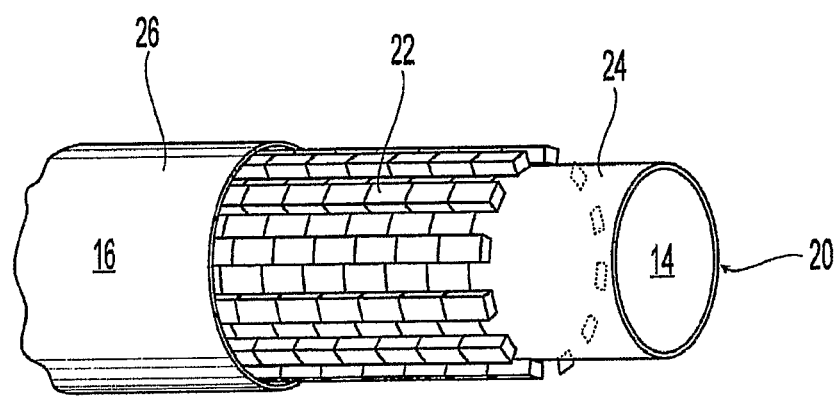
FIG. 3B is an exploded perspective view of the stent graft of FIG. 3.
Figure 3A:
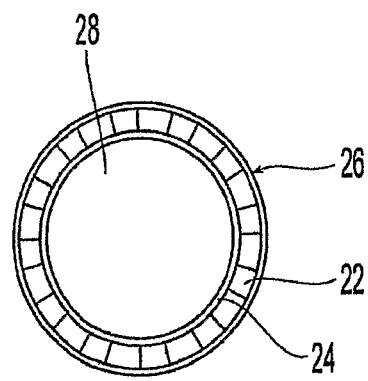
FIG. 3A is a cross-sectional view of the stent graft of FIG. 3 along line 3A-3A.

Referring now to FIGS. 3-3A, shown is a preferred embodiment of an encapsulated stent or "stent-graft" 10. The stent-graft 10 can generally include a tubular member 12 having an interior surface 14 and an exterior surface 16 which are contained between first and second ends 18, 20. An elongated radiopaque marker 6 is preferably provided on the exterior surface 16. As illustrated in FIGS. 3, 3A and 3B, the tubular member 12 preferably includes a balloon or pressure expandable tubular shaped support member 22 which is loaded over a first biocompatible flexible tubular member 24 that is held on a mandrel (not shown). A second biocompatible flexible tubular member 26 is then preferably loaded over the first biocompatible tubular member/support member combination 22, 24. The tubular shaped support member 22 preferably includes a stent similar to that shown or described in any one of U.S. Pat. Nos. 4,733,665; 6,053,941; 6,053,943; 5,707,386; 5,716,393; 5,860,999; and 6,572,647 each of which is incorporated in its entirety by reference. The stent utilized for the member 22 can be balloon expandable stent, self-expanding stent or memory-shaped plastic stent. The tubular members 24, 26 are preferably fused together to encapsulate the support member 22.

The tubular members 24, 26 of stent-graph 10 are preferably formed in a manner substantially similar to the extruded graph device 100 described above. In particular, the first and second biocompatible flexible tubular members 24, 26 are preferably made by extruding a billet of expanded polytetrafluoroethylene (ePTFE). Alternatively, the first and second biocompatible flexible tubular members 24, 26 may also be made of unexpanded polytetrafluoroethylene (PTFE). The tubular member 26 is preferably extruded along with a radiopaque material to form at least one elongated radiopaque marker 6 embedded in the outer surface of the tubular member 26. Alternatively or in addition to, the tubular member 24 can also be extruded along with a radiopaque material to form at least one elongated radiopaque marker embedded in the outer surface of the tubular member 24. Further, the pressure expandable tubular shaped support member 22 may be made of any material having the strength and elasticity to permit radial expansion and resist radial collapse such as silver, titanium, stainless steel, gold, and any suitable plastic material capable of maintaining its shape and material properties at various sintering temperatures for PTFE or ePTFE.

Shown in FIG. 3A is a cross-sectional view of the stent-graft 10 of FIG. 3 prior to fusing the graft or tubular members 24, 26 to the expansion member 22. The first biocompatible flexible tubular member 24, preferably made of unsintered ePTFE, forms the innermost layer or luminal surface of the stent-graft 10, and covers the lumen 28 of the stent-graft 10, thereby providing a smooth, inert biocompatible blood flow surface. The tubular support member 22, preferably a stent or similarly constructed structure, forms the middle layer located at the center of the stent-graft 10. Finally, the second biocompatible flexible tubular member 26, which is also preferably made of unsintered ePTFE, forms the outermost layer or abluminal surface of the stent-graft 10.

To form the stent-graft 10, the tubular shaped members 24, 22, and 26 can be loaded onto one another. Pressure is applied to the graft/stent/graft assembly in order to fuse the first and second biocompatible flexible tubular members 24, 26 to one another through the openings contained within the tubular support member 22. Where the tubular support member 22 is a stent frame, the first and second ePTFE tubular members 24, 26 are fused to one another through the openings between the struts of the stent. The graft/stent/graft assembly is then heated at sintering temperatures to form a physical bond between the ePTFE layers. The resulting prosthesis is an unexpanded stent encapsulated within ePTFE layers, or specifically, an unexpanded stent having ePTFE layers on its luminal and abluminal surfaces in which the stent and ePTFE layers are inseparable. Alternatively, the prosthesis can include hydroxyapatite on both its luminal and abluminal surfaces. Further, the ePTFE layers may also be fused or joined together around the ends of the unexpanded stent thereby entirely encasing the stent within ePTFE in both the radial and longitudinal directions. The resulting stent-graft 10 can be loaded onto a suitable delivery device such as, for example, U.S. Pat. No. 6,756,007, which is incorporated in its entirety by reference. The stent-graft 10 may advantageously be used in a variety of medical applications including intravascular treatment of stenoses, aneurysms or fistulas; maintaining openings in the urinary, biliary, tracheobronchial, esophageal, renal tracts, vena cava filters; repairing abdominal aortic aneurysms; or repairing or shunting damaged or diseased organs such as, for example, Transjugular Intrahepatic Portosystemic Shunt (TIPS).

Figure 4:
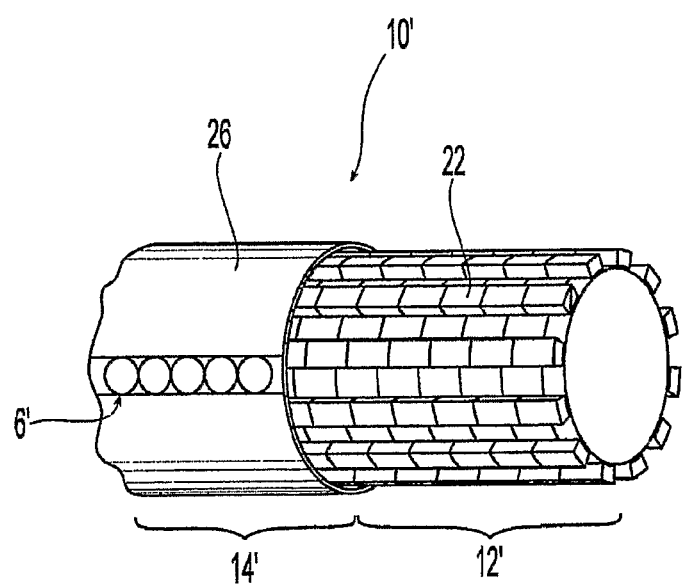
FIG. 4 is a perspective view of another embodiment of a stent graft having a longitudinal radiopaque marker.

Procedures like TIPS can use an alternative embodiment of the stent-graft 10 as shown in FIG. 4. Shown in FIG. 4 is a stent-graft 10' having a bare stent portion 12' embedded in a stent-graft, encapsulated or covered portion 14', i.e., a "hybrid" stent-graft. A surgical procedure using the hybrid or stent-graft 10' may require determination of where the covered portion 14' ends during the procedure in order to allow blood flow through the uncovered stent-graft portion 12'. The encapsulated portion 14' of the hybrid stent graft 10' is preferably formed in a manner substantially similar for forming the stent-graft 10 as described above so as to include extrusion of at least an outer ePTFE or PTFE member 26' with an elongated radiopaque material to form the radiopaque marker 6'. Accordingly, the radiopaque marker or strip 6' on the covered portion 14' of the stent 10' provides a medical practitioner with a visual cue as to the actual position of the covered portion while the implantable prosthesis is inside a mammalian body. In addition, the radiopaque marker or strip 6' provides by its proximity, the position of the uncovered portion 12' of the hybrid stent-graft 10' to determine placement of the entire stent-graft 10' during and subsequent to a surgical procedure. Moreover, the radiopaque strip 6' can eliminate the need for "spoon" or bead-type markers used at the non-encapsulated ends of the stent 10'.

Figure 5:
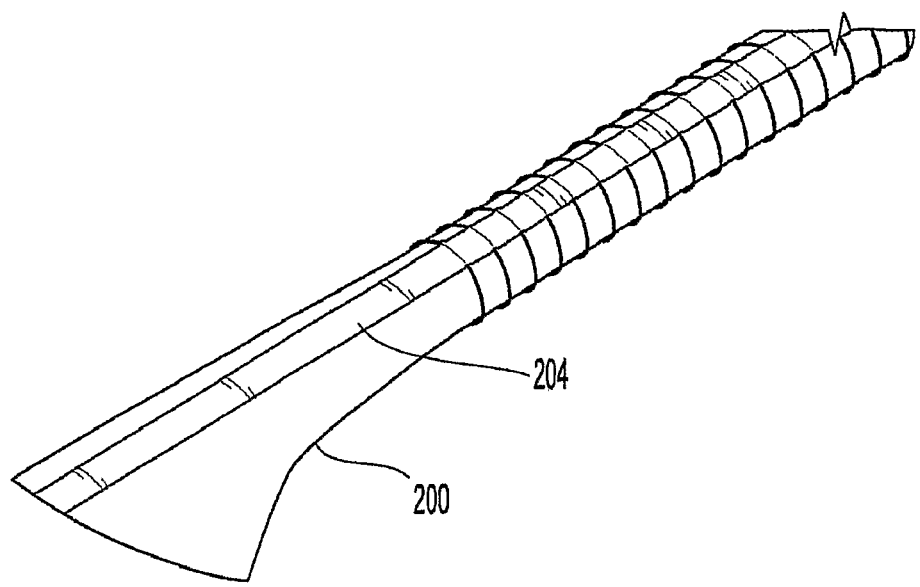
FIGS. 5 and 6 are additional embodiments of a graft device having a radiopaque marker.
Figure 6:
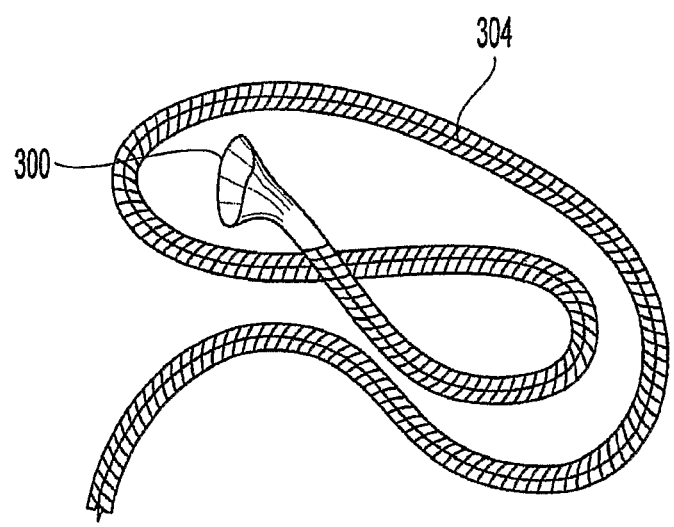

Referring to FIGS. 5 and 6, shown are alternative embodiments of a graft, namely vascular bypass grafts 200 and 300 having a radiopaque elongation, marker, or strip embedded in the outer surface. Vascular bypass graft 200 is configured for desired blood flow characteristics for applications above the knees, whereas bypass graft 300 is configured for blood flow characteristics below the knee. Regardless of the structural configurations and applications of the bypass grafts 200 and 300, the grafts 200, 300 can be preferably formed by extruded ePTFE material along with a radiopaque paste as described above to provide the elongated radiopaque markers or strips 204, 304. That is, a radiopaque paste can be embedded or incorporated by extrusion with the synthetic non-metallic material (e.g., Dacron, polyester, PTFE, ePTFE, polyurethane, polyurethane-urea, siloxane, and combinations thereof) to form grafts 200 and 300 with a radiopaque strip 204, 304 along at least one of the luminal and abluminal surfaces of the grafts (200 or 300). The material or combinations of materials used (e.g., Dacron, polyester, PTFE, ePTFE, polyurethane, polyurethane-urea, siloxane, and combinations thereof) can include surface modifying additives or other materials. Examples of various grafts are shown and described in U.S. Pat. Nos. 6,203,735; 6,039,755; and 6,790,226, each of which is incorporated in its entirety by reference.

Figure 7:
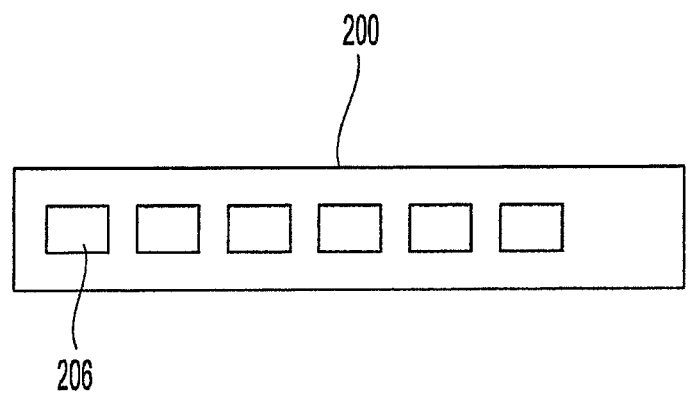
FIG. 7 is another embodiment of a graft device having a radiopaque marker.

Shown in FIG. 7 is another embodiment of the graft device 200. In the device 200, the graft material can be formed in a manner as previously described above using PTFE. However, the radiopaque marker 206 is not extruded with the graft material. Instead, the radio-opaque marker 206 is preferably printed on the extruded PTFE forming the tube of the device 200 by a suitable printing technique, such as, for example, engraving, mono-type, offset, cliché transfer, ink-jet or gliceé printing. The radio-opaque marker 206 can be a radio-opaque ink such as, for example, the ink produced by CI Medical, Inc. of Norton, Mass. Preferably, the radiopaque ink is tungsten based in which tungsten is mixed as a radio-opaque component into the ink. In one embodiment, an ink composition for an orientation line for an ePTFE surface includes a suitable polymeric binder that adheres well to an ePTFE surface, a biocompatible dye or pigment, a radiopaque material and a solvent that dissolves the polymeric binder. In addition, the ink composition may contain inorganic white solid materials such as titanium dioxide (to adjust ink shade) and a viscosity modifier. Although many pigments or dyes may be used to make the orientation line, pigments or dyes that have a long history of human implantation are most preferred. The preferred color compounds in the ink include, but are not limited to: (Phthalocyaninato(2-)) copper, D&C Blue No. 9, D&C Green No. 5, Chlorophyllin-copper complex, oil soluble, Chromium-cobalt-aluminum oxide, Ferric ammonium citrate, D&C Blue No. 5, FD&C Blue No. 2, D&C Green No. 6, Titanium dioxide, carbon, Iron oxide, and the like. (Phthalocyaninato(2-)) copper is the most preferred green compound. The color of the ink (e.g., black, blue, etc.) may be determined by viewing under a light having a temperature of about 6500 degrees Kelvin. Hence, in this embodiment, the lines are not only visible to the unaided human eyes, they are also visible to the human eyes with a suitable fluoroscope imager.

Figure 8:
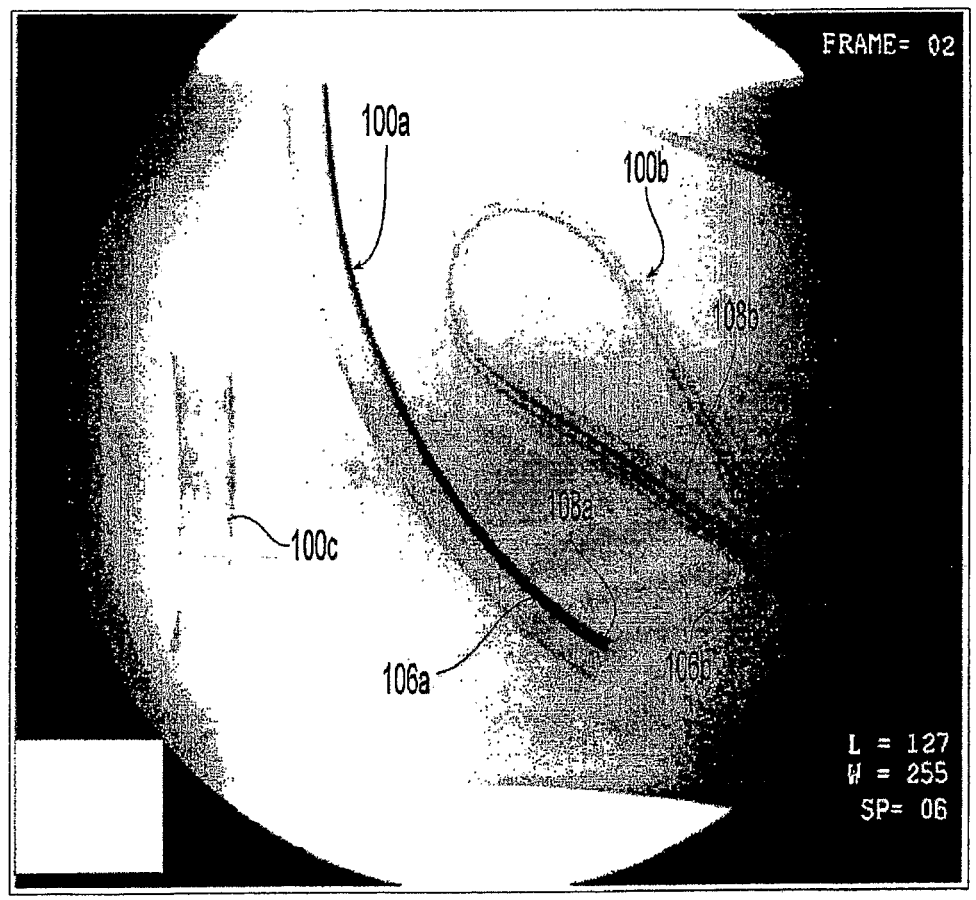
FIG. 8 is a fluoroscopic view of different embodiments of a bare stent and graft devices having a radiopaque marker.

With reference to FIG. 8, it has been demonstrated that various physical embodiments of the device can be viewed under fluoroscopic examination. In FIG. 8, two graft devices 100A and 100B were provided along with a stent-graft 100c (commercially available under the trade name Fluency®) as referential datum for visibility under a fluoroscope imaging device through an Aluminum plate of 15 millimeters thickness. The reference stent-graft 100c was utilized with radiopaque ink that had 50% tantalum and 50% polycarbonate polyurethane as polymeric binder. The ink solution/dispersion was prepared by dissolving the polymer in tetrahydrofuran solvent. The dispersion was hand painted using a paint brush to create a circular band on the stent graft surface. The band is slightly visible under fluoroscope so that the reference stent-graft 100c acts as referential datum as to the minimum radiopacity required. The aluminum plate is utilized to simulate the density of biological tissues by interposition of the plate (not shown) between the fluoroscope and the subject graft device. That is, the image of the reference stent-graft 100c in FIG. 8 provides for an indication of the radiopacity of the stent as compared to the background environment on which the stent graft is placed in. Further, by having the Fluency stent graft in the image, a referential datum as to the effectiveness of the radiopaque line of the preferred embodiments is provided without resorting to observers with specialized training or machine visions. Consequently, as long as an ordinary observer can determine that the lines provided by the graft of the preferred embodiment in a fluoroscopic display medium has a darker or higher contrast image than the reference stent-graft 100c, then the radiopacity of the line would be deemed to be greater than a minimum level needed for the line to function as a radio-opaque marker in a mammalian body. Alternatively, a machine vision with the ability to recognize discrete levels of contrast can be utilized to provide an objective indicator of the effectiveness of the radiopacity of the radiopaque lines.

The graft device 100a was provided with two lines 106a and 108a where each line can be a combination of two different radiopaque materials: (1) Barium Sulfate and (2) Tantalum. Even though both lines are formed of different materials, both materials form generally similar solid black lines of radiopacity greater than the referential bare stent in a suitable imaging device, which is a black-and-white photographic print, as shown in FIG. 8. Alternatively, graft 100b was provided with two lines 106b and 108b where 106b is made of 60% by weight Barium Sulfate material and a suitable colorant (e.g., cobalt blue). This line appears blue to the naked eye and is radio-opaque. The line 108B is made using 60% (by weight) of Tantalum powder and is black in color. The tantalum provides the black coloring and generally no coloring agent is needed. These lines demonstrate that a clinician (or even an ordinary observer without any specialized training) would be able to observe and determine whether the graft device has been moved about in the body subsequent to implantation into an undesirable configuration by observing the orientation of such line on a fluoroscopic display medium (paper or graphical display monitor). For example, where the graft has twisted about its own axis, the display medium would show that the line forms a spiral, which is partly shown for graft 100A. Where the graft has rotated about an axis transverse to a longitudinal axis of the graft, i.e., a kink, the display medium would show an intersecting point rather than a smooth inflection curve, shown here in FIG. 8 for graft 100B.

Although the graft device 100 has been described in relation to specific examples noted above, it should be emphasized that variations in the configuration or composition of ePTFE, radiopaque marker, stent framework, and other design parameters can be utilized with the graft device 100. For example, the weight percentage of either the tantalum powder or the Barium Sulfate in the graft device can vary. The percentage of radio-opaque composition in the graft will depend on the amount of radio-opacity needed for a given medical application and the amount of graft expansion subjected during manufacturing. The percentage of radio-opaque element such as tantalum or Barium Sulfate will very from 5% to 70% most preferably from 20% to 60% and even more preferably from 50-60%. Finally, other types of bioactive agents can also be combined with the radiopaque materials described herein for the graft and the stent graft. The bioactive agents include (but are not limited to) pharmaceutic agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) $II_b/III_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

Furthermore, the radiopaque marker, when configured as a strip or substantially straight line provides additional visual cues to the practitioner or clinician beyond graft location. Specifically, the straight line radiopaque marker can indicate whether there is any twisting of the graft during and subsequent to the implantation procedure. This feature is believed to be advantageous in that it allows for a clinician to determine with certainty whether the prosthesis has been implanted optimally in the body without kinking or twisting. That is, prior to the development of the prosthesis as described herein, movements of the arms and legs could cause the implanted prosthesis to kink or twist so as to restrict blood flow through the prosthesis without the clinician being aware of such adverse configurations after the implantation has been completed. The prosthesis, as described herein, allows the clinician to achieve an advantageous technique by ensuring that the prosthesis implanted by the clinician is properly configured inside the mammalian body. Alternatively, other types of indicia (e.g., date of manufacture, manufacture etc.,) can be provided by printing the radiopaque material onto the graft. The radio-opaque lines can also be encoded such as are used, for example, in bar coding of commercial goods. For example bar code, a series of black and white lines with certain thickness and heights can be interpreted by the machines as digital code which can be used in a computer database.

As used herein, the singular form of "a," "an," and "the" include the plural referents unless specifically defined as only one. While the present invention has been disclosed with reference to certain preferred embodiments, numerous modifications, alterations, and changes to the described embodiments are possible without departing from the sphere and scope of the present invention, as defined in the appended claims. Moreover, where methods, processes and steps described above indicate that certain events occurring in certain order, those skilled in the art would recognize that the ordering of steps may be modified and that such modifications are within the variations of the described embodiments. Accordingly, it is intended that the present invention not be limited to the described embodiments, but that it have the full scope defined by the language of the following claims, and equivalents thereof.

We claim:

1. A graft device comprising:
   an extruded layer of synthetic non-metallic material having a first surface and a second surface spaced apart from the first surface; and
   a co-extruded first radiopaque marker and a coextruded second radiopaque marker each at least partially embedded in the layer, the first radiopaque marker being formed of a first radiopaque material and the second radiopaque marker being formed of a second radiopaque material different from the first radiopaque material.

2. The graft device according to claim 1, wherein the first radiopaque marker defines a portion of the first surface.

3. The graft device according to claim 1, wherein the first radiopaque marker defines a portion of the second surface.

4. The graft device according to claim 1, wherein the first radiopaque marker is disposed between the first and second surfaces.

5. The graft device according to claim 1, wherein the synthetic non-metallic material comprises a material selected from a group consisting essentially of Dacron, polyester, PTFE, ePTFE, polyurethane, polyurethaneurea, siloxane, and combinations thereof.

6. The graft device according to claim 1, wherein the first radiopaque marker is formed from a paste having about 20% to about 60% tantalum powder.

7. The graft device according to claim 1, wherein the first radiopaque marker is formed from a paste having about 20% to about 40% Barium Sulfate.

8. The graft device according to claim 7, wherein the Barium Sulfate is mixed with a biocompatible coloring agent.

9. The graft device according to claim 8 wherein the coloring agent is green, blue or black colored.

10. The graft device according to claim 9 wherein the coloring agent is cobalt blue.

11. The graft device according to claim 1, wherein the graft device has a length extending axially from end to end, and the first radiopaque marker comprises a first continuous line that extends along a majority of the length of the graft device.

12. The graft device according to claim 11, wherein the second radiopaque marker comprises a second continuous line parallel to the first continuous line, the second continuous line extending along the majority of the length of the graft device.

13. The graft device according to claim 12, wherein one of the first continuous line is formed from a paste including Barium Sulfate and the second continuous line is formed from a paste including tantalum powder.

14. The graft device according to claim 12, wherein the layer is tubular in shape, and wherein the first continuous line and the second continuous line are formed within a same circumferential third of the layer.

15. A device comprising:
a stent frame;
an extruded synthetic non-metallic material that surrounds a portion of the stent frame, the synthetic non-metallic material having first and second surfaces; and
a first co-extruded radiopaque strip and a second coextruded radiopaque strip embedded in the nonmetallic material, the first radiopaque strip and the second radiopaque strip each formed from a combination of at least two different radiopaque materials.

16. A method of forming a graft device comprising:
extruding a synthetic non-metallic material so as to form a member having a first surface and a second surface spaced apart from the first surface, wherein
extruding includes extruding a first radiopaque material into a first continuous line and extruding a second radiopaque material into a second continuous line such that the first radiopaque material and the second radiopaque material are at least partially embedded in the non-metallic material, the second radiopaque material being different from the first radiopaque material.

17. The method according to claim 16, wherein the member has a length extending axially from a first end to a second end, and extruding further includes extruding the first radiopaque material and the second radiopaque material such that the first continuous line extends along a majority of the length of the member and the second continuous line is parallel to the first continuous line and extends along a majority of the length of the member.

18. The graft device according to claim 16, wherein the synthetic non-metallic material comprises PTFE resin compounded with a hydroxyapatite material, and extruding the synthetic non-metallic material comprises extruding the PTFE resin compounded with the hydroxyapatite material.

19. A graft device comprising:
a layer of synthetic non-metallic material having a first surface and a second surface spaced apart from the first surface; and
a first orientation line and a second orientation line disposed along at least one of the first and second surfaces, the first orientation line formed by a radiopaque marker of a first radiopaque material mixed with a coloring agent coextruded with the layer of synthetic non-metallic material, and the second orientation line formed by a radiopaque marker of a second radiopaque material different from the first material that is not mixed with a coloring agent but is coextruded with the layer of synthetic nonmetallic material.

20. The graft device of claim 19, wherein the first orientation line and the second orientation line form a parallel pair of lines extending along a majority of an end to end axial length of the nonmetallic material.

* * * * *